(12) United States Patent
Ma et al.

(10) Patent No.: US 7,118,356 B2
(45) Date of Patent: Oct. 10, 2006

(54) FLUID PUMP WITH A TUBULAR DRIVER BODY CAPABLE OF SELECTIVE AXIAL EXPANSION AND CONTRACTION

(75) Inventors: Jan Ma, Singapore (SG); Yin Chiang Boey, Singapore (SG)

(73) Assignee: Nanyang Technological University, Singapore (SG)

( * ) Notice: Subject to any disclaimer, the term of this patent is extended or adjusted under 35 U.S.C. 154(b) by 323 days.

(21) Appl. No.: 10/611,306

(22) Filed: Jul. 1, 2003

(65) Prior Publication Data

US 2005/0017603 A1 Jan. 27, 2005

Related U.S. Application Data

(60) Provisional application No. 60/415,844, filed on Oct. 2, 2002, provisional application No. 60/416,505, filed on Oct. 3, 2002.

(51) Int. Cl.
*F04B 17/00* (2006.01)
*A61N 1/362* (2006.01)
*A61M 1/00* (2006.01)

(52) U.S. Cl. ............... 417/410.1; 417/410.2; 417/412; 417/423.1; 417/423.14; 417/572; 417/48; 604/151; 604/152; 604/131; 600/16; 600/17; 600/18

(58) Field of Classification Search ............. 417/410.2, 417/423.1, 423.14, 572, 48, 410.1, 412; 604/151, 152, 131; 600/16, 17, 18
See application file for complete search history.

(56) References Cited

U.S. PATENT DOCUMENTS

| 3,305,825 | A | * | 2/1967 | Godbey | 367/85 |
|---|---|---|---|---|---|
| 5,147,281 | A | | 9/1992 | Thornton et al. | |
| 5,370,509 | A | * | 12/1994 | Golding et al. | 417/423.1 |
| 5,761,782 | A | * | 6/1998 | Sager | 29/25.35 |
| 5,798,600 | A | * | 8/1998 | Sager et al. | 310/330 |
| 5,947,892 | A | * | 9/1999 | Benkowski et al. | 600/16 |
| 6,080,133 | A | * | 6/2000 | Wampler | 604/131 |
| 6,388,364 | B1 | | 5/2002 | Cremer et al. | |
| 6,527,521 | B1 | * | 3/2003 | Noda | 417/355 |
| 6,592,335 | B1 | * | 7/2003 | Rosefsky | 417/53 |

FOREIGN PATENT DOCUMENTS

| EP | 0 173 661 | 3/1986 |
|---|---|---|
| EP | 1 215 737 | 6/2002 |
| GB | 2 002 052 | 2/1979 |

(Continued)

OTHER PUBLICATIONS

"Single-tube three dimensional scanner for scanning tunneling microscopy" by Binnig et al; *Rev. Sci. Instrum.* 57 (Aug. 1986); pp. 1688-1689.

(Continued)

*Primary Examiner*—Tae Jun Kim
*Assistant Examiner*—Ryan Gillan
(74) *Attorney, Agent, or Firm*—Knobbe, Martens Olson & Bear LLP

(57) ABSTRACT

A fluid pump for pumping fluid. The fluid pump includes a driver having a substantially tubular shaped body defining a body axis and, a number of elements circumferentially spaced around the body. Each element is responsive to a signal to so as cause a corresponding portion of the body to expand or contract in a direction substantially parallel to the tube axis. The pump also includes an urging member positioned in a flow path. In use, the urging member is coupled to the driver such that selective expansion and/or contraction of the body causes the urging member to rotate, thereby urging fluid along the flow path.

32 Claims, 9 Drawing Sheets

FOREIGN PATENT DOCUMENTS

| | | |
|---|---|---|
| GB | 2 054 756 | 2/1981 |
| JP | 1996336967 A | 12/1996 |
| JP | 2002252391 A | 9/2002 |

OTHER PUBLICATIONS

"An ultrasonic micromotor using a bending cylindrical transducer based on PZT thin film" by Morita et al; *Sensors and Actuators* A 50 (1995); pp. 75-80.

"A cylindrical shaped micro ultrasonic motor utilizing PZT thin film (1.4mm in diameter and 5.0mm long stator transducer)" by Morita et al; *Sensors and Actuators* 83 (2000); pp. 225-230.

"A Cylindrical Micro Ultrasonic Motor Using PZT Thin Film Deposited by Single Process Hydrothermal Method ($\phi$ 2.4mm, L=10mm Stator Transducer)" by Morita et al; *IEEE Transactions on Ultrasonics, Ferroelectrics, and Frequency Control*, vol. 45, No. 5 (Sep. 1998); pp. 1178-1187.

"A Cylindrical Ultrasonic Micro Motor Based on PZT Thin Film" by Kurosawa et al; *IEEE Ultrasonics Symposium* (1994); pp. 549-552.

"A micro ultrasonic motor fabricated by hydrothermal method (1.4mm in diameter and 5mm in length stator transducer)" by Morita et al; *IEEE Ultrasonic Symposium* (1998); pp. 671-674.

"Electrophoretic Deposition of Advanced Ceramics" by Cheng et al; *Processing and Fabrication of Advanced Materials* VIII (2000); pp. 517-524.

"Properties of Modified Lead Zirconate Titanate Ceramics Prepared at Low Temperature (800° C.) by Hot Isostatic Pressing" by Li et al; *J. Am. Ceram. Soc.* 83 (2000); pp. 955-957.

"Design of a Cylindrical Ultrasonic Micromotor to Obtain Mechanical Output" by Morita et al; *Jpn. J. Appl. Phys.* vol. 35 (1996); pp. 3251-3254.

"Cylindrical Micro Ultrasonic Motor Utilizing Bulk Lead Zirconate Titanate (PZT)" by Morita et al; *Jpn. J. Appl. Phys.* vol. 38 (1999); pp. 3347-3350.

"Effect of Shear Stress on Sintering" by Rahaman et al; *J. Am. Ceram. Soc.* 69 (1986); pp. 53-58.

"Loss Mechanisms in Piezoelectrics: How to Measure Different Losses Separately" by Uchino et al; *IEEE Transactions on Ultrasonics, Ferroelectrics, and Frequency Control* vol. 48 (2001); pp. 307-321.

"Compact Ultrasonic Rotary Motors" by Uchino et al; *Ferroelectrics* vol. 257 (2001); pp. 3-12.

"Analysis of Bending Displacement of Lead Zirconate Titanate Thin Film Synthesized by Hydrothermal Method" by Ohba et al; *Jpn. J. Appl. Phys.* vol. 32 (1993); pp. 4095-4098.

"Piezoelectric Properties of Niobium-Doped $[Pb(Sc_{1/2}Nb_{1/2})_{1-x}Ti_x]O_3$ Ceramics Material near the Morphotropic Phase Boundary" by Yamashita et al; *Jpn. J. Appl. Phys.* vol. 33 (1994); pp. 4652-4656.

"Piezoelectric tubes and tubular composites for actuator and sensor applications" by Zhang et al; *J. Mater. Sci.* 28 (1993); pp. 3962-3968.

"Design and Fabrication of a High Performance Multilayer Piezoelectric Actuator with Bending Deformation" by Yao et al; *IEEE Transactions on Ultrasonics, Ferroelectrics, and Frequency Control* vol. 46 (1999); pp. 1020-1027.

"Electromechanical Properties of Composite Bending-Type Transducers" by Marutake et al; *Jpn. J. Appl. Phys.* vol. 34 (1995); pp. 5284-5287.

"$Ba(Ti_{1-5/4x}Nb_x)O_3$ Relaxor Ferroelectrics" by Zhang et al; *Ferroelectrics Letters* vol. 29 (2002); pp. 125-130.

\* cited by examiner

FLUID PUMP WITH A TUBULAR DRIVER BODY CAPABLE OF SELECTIVE AXIAL EXPANSION AND CONTRACTION

RELATED APPLICATIONS

This application claims the benefit of U.S. provisional applications 60/415,844 filed Oct. 2, 2002 entitled "PUMP" and 60/416,505 filed Oct. 3, 2002 entitled "PIEZOELECTRIC TUBES" which are both incorporated herein in their entirety by reference.

BACKGROUND OF THE INVENTION

1. Field of the Invention

The invention relates to a pump for pumping fluid, and in particular, to a piezoelectric axial pump suitable for use as a heart pump, or the like.

2. Description of the Related Art

The reference to any prior art in this specification is not, and should not be taken as, an acknowledgement or any form of suggestion that the prior art forms part of the common general knowledge.

Currently, tens of thousands of patients suffer from heart failure worldwide. For example, a patient in the U.S. has suffered with heart failure for most of her adult life. Diagnosed at age 25, doctors attribute her heart failure to a hereditary condition. Her father shared the same disease and died at age 32 more than 20 years ago. Development of a heart assist device that can be implanted into the body and help the heart to pump the blood is necessary in aiding patients with such conditions.

Conventionally heart pumps are implemented in the form of electromagnetic pumps. However, pumps of this form suffer from a number of problems, such as the fact that the apparatus is relatively heavy in weight, has a large size and can be affected by external magnetic fields. Furthermore, the operation of the pump can lead to the generation of vortices in the blood.

It is therefore necessary to develop a heart pump that can assist the heart to pump the blood to the whole body at heart failure. In particular, it is desirable that the pump is small, light-weight, has a low power consumption, does not generate vortices in the pumped blood and is minimally affected by the external factors, such as magnetic fields.

An example of a piezoelectric rotator is shown in U.S. Pat. No. 6,388,364. In this example, the rotator uses piezoelectric members that operate to expand and contract in a predetermine manner to cause rotation of a ring. However, the performance of such configurations is limited. In particular, the piezoelectric members extend across the ring, thereby restricting the usefulness of this form of motor in fluid pumping applications. Furthermore, rotators of this form tend to generate rotational torques, and are therefore generally unsuitable for fluid pumping applications.

SUMMARY OF THE INVENTION

In a first broad form the invention provides a fluid pump for pumping fluid, the fluid pump including: a flow path, a driver having a substantially tubular shaped body defining a body axis and a number of elements circumferentially spaced around the body, each element being responsive to a signal to cause a corresponding portion of the body to expand or contract in a direction substantially parallel to the tube axis, and an urging member positioned in the flow path, the urging member being coupled to the driver such that selective expansion and/or contraction of the body causes the urging member to rotate, thereby urging fluid along the flow path in use.

In one embodiment, the elements are piezoelectric elements. In one embodiment, The elements extend substantially along the length of the body. In one embodiment, The tubular shaped body generally has a diameter of less than 0.1 m, and a length of less than 1 m.

In one embodiment, The body is formed from piezoelectric material, with each piezoelectric element being formed from a common electrode mounted on an inner surface of the tubular body and a respective electrode mounted on an outer surface of the tubular body.

In another embodiment, the body can be formed from a double layered piezoelectric material, each piezoelectric element being formed from a common electrode positioned between the layers, a first set of respective electrodes mounted on an inner surface of the body and, a second set of respective electrodes mounted on an outer surface of the body.

Each electrode can be formed from a thin metal film having a thickness of less than 0.001 m.

In one embodiment, The pump further includes a controller coupled to the elements, the controller being adapted to generate electrical signals thereby causing the selective expansion and contraction of the elements.

In one embodiment, The elements are arranged in pairs, each pair being positioned in circumferential opposition, the controller being adapted to generate signals to thereby selectively activate an element pair such that one of the elements expands and the other element contracts.

In one embodiment, The controller is adapted to activate the element pairs in turn, to thereby cause elements to expand and contract in a circumferential sequence.

The pump can be adapted to generate signals having a selected frequency the signals applied to each element in the element pair having a phase difference of 180°.

In this case, the controller can be coupled to a DC power source to receive an input signal of up to 1000 V, the controller being adapted to generate signals of between 1 to 10000 Vp-p and a selected frequency of up to 40 MHz.

In one embodiment, The urging member includes a shaft defining a shaft axis that extends along the flow path and a blade extending radially from the shaft, the blade extending circumferentially around the shaft and along the shaft axis, such that rotation of the shaft causes the blade to urge fluid in a direction substantially parallel to the shaft axis.

In one embodiment, The blade extends along the shaft so as to define a thread, with the pitch of the thread varying along the length of the shaft.

The shaft may be substantially tubular, and the blade extending radially inwardly toward the shaft axis. Alternatively, the shaft can be substantially cylindrical, the blade extending radially outwardly from the shaft. The shaft may also be tapered.

In one embodiment, The urging member includes end caps for coupling the shaft to the driver.

In this embodiment, Each end cap generally has a substantially frustroconical shape, having a cone angle of between 60° and 70°. In one embodiment, The end caps are coupled to the shaft such that the end caps are urged against ends of the piezoelectric elements. In one embodiment, at least one of the end caps is coupled to the shaft by a resilient member, the resilient member being adapted to urge the end cap against a respective end of the piezoelectric elements.

In this case, the resilient member can be a spring having a spring constant of between 0.005 and 0.02 kg/mm.

In one embodiment, The pump is coupled to a circulatory system to pump blood, or the like.

In a second broad aspect, the invention provides a fluid pump for pumping fluid, the fluid pump including a flow path, a driver having: a substantially tubular shaped body defining a body axis and a number of elements circumferentially spaced around the body, each element being responsive to a signal to cause a corresponding portion of the body to expand or contract in a direction substantially parallel to the tube axis, the driver being arranged in the flow path such that selective expansion and/or contraction of the body urges fluid along the flow path in use.

In one embodiment, the driver may be similar to the driver described above with respect to the first broad form of the invention.

Alternatively, the elements may be adapted to extend circumferentially around the body, with a number of elements being provided along the body.

In one embodiment, an inner surface of the driver can be provided with a profile, to thereby aid the urging of fluid.

BRIEF DESCRIPTION OF THE DRAWINGS

An example of the invention will now be described with reference to the accompanying drawings, in which.

DETAILED DESCRIPTION OF THE PREFERRED EMBODIMENT

Figure 1:
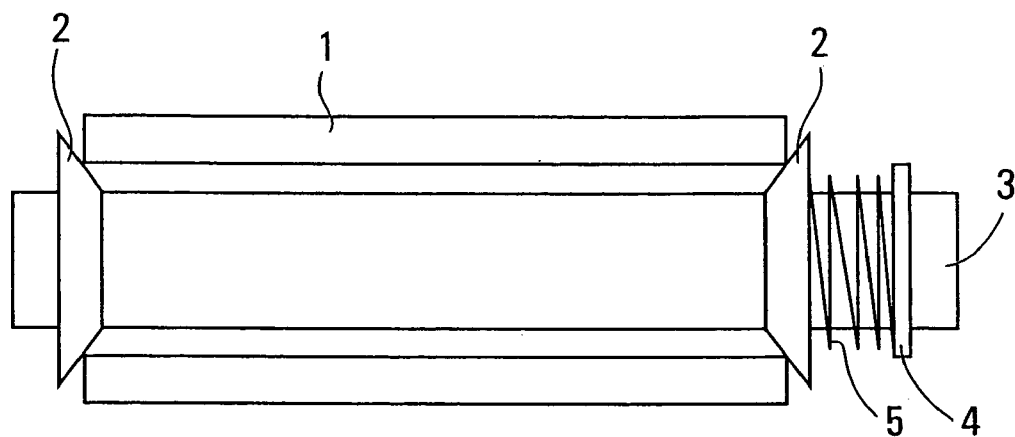
FIG. 1 is a schematic diagram of a pump according to the invention.

An example of a pump according to the invention will now be described with reference to FIG. 1.

In particular, the pump is formed from a tubular shaped transducer 1 coupled via two end caps 2 to an inducer 3. The end caps 2 are held under tension via a retaining nut 4 and a spring 5, as shown.

In use, excitation signals are applied to the transducer causing selective contraction and/or expansion of the transducer. The expansion or contraction of the transducer is used to induce an oscillatory motion in the transducer ends, which causes the inducer to rotate under the control of the applied signals. The inducer is configured such that rotation of the inducer causes fluid to be urged along a flow path, thereby providing a pumping action.

The manner in which this is achieved will now be described in more detail, with respect to an example in which the transducer is piezoelectric transducer.

Figure 2:
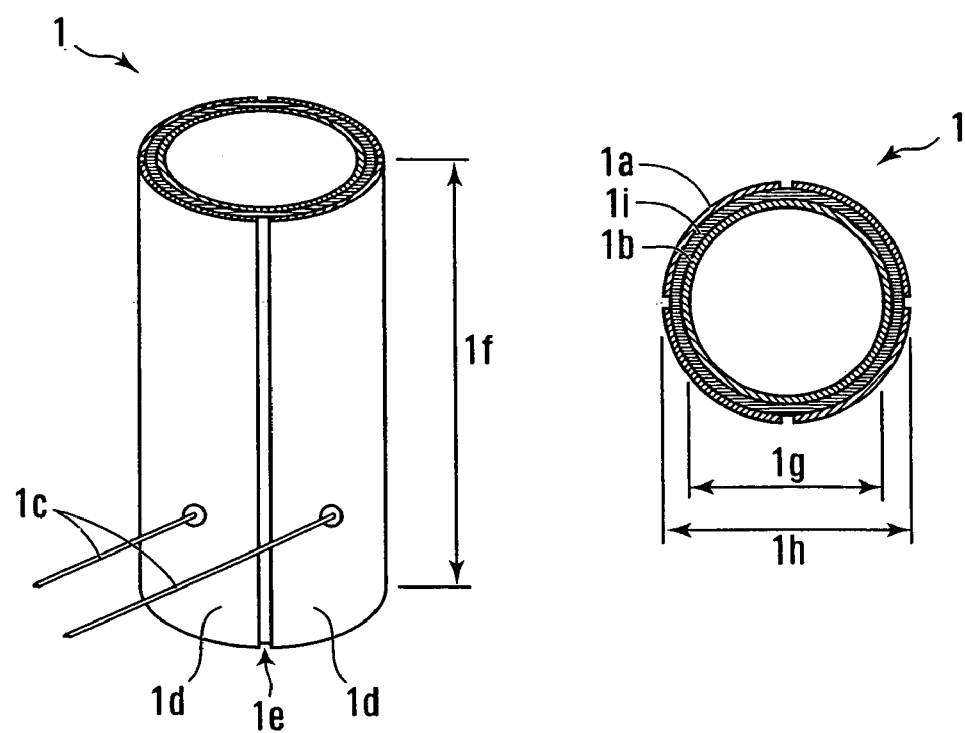
FIG. 2 is a schematic diagram of an example of piezoelectric transducer.

One embodiment of a piezoelectric transducer is shown in more detail in FIG. 2. As shown, the piezoelectric transducer 1 is formed from a piezoelectric tube 1*i* having an inner surface coated with an inner electrode 1*b*, and an outer surface coated with an outer electrode 1*a*. In one embodiment, the outer electrode 1*a* is divided into four portions, which are circumferentially spaced around the outer surface of the tube 1*i*, and which are separated by the gaps 1*e*. In this embodiment, each electrode portion extends substantially along the length of the tube 1*i*, as shown.

The dimensions of the piezoelectric tube can be selected and optimized according to the practical application. However, typically the dimensions are within the following ranges: Outer diameter 1*h* ranges from 1 mm to 25 mm; Inner diameter 1*g* ranges from 0.1 mm to 24 mm; and Length 1*f* ranges from 5 mm to 250 mm;

In order to provide the piezoelectric effect, the tube 1*i* is formed from a piezoelectric material such as PZT (Lead Zirconate Titanium), modified PZT, or the like. It is preferable that the tube is formed from a mechanically hard material having a high piezoelectric constant d31 and mechanical quality factor Qm. An example of the manner of manufacture of such a device is provided in our copending application entitled "Piezoelectric Tubes" (filed as Ser. No. 60/416,505, filed Oct. 3, 2002) which is incorporated herein in its entirety by reference.

In this embodiment, the technique involves forming a suspension of piezoelectric ceramic particles, such as lead zirconate titanate (PZT), doped lead zirconate titanate (PZT), BaTiO3, or the like, in a solvent medium. Typically organic solvents, such as ethanol and acetone, are used, although alternative solvents, such as water, may also be used if appropriate. A rod is positioned in the fluid medium, with the particles being deposited on the rod using electrophoresis.

The deposited layer is then heat treated by heating in a furnace at between 500° C. and 1200° C., to thereby solidify the particle layer and burn away the rod, to thereby a tube formed from the intact particle layer. The tube is then sintered at temperatures between 850° C. and 1300° C. to form a dense ceramic tube.

The tube is then allowed to cool, before having the closed end removed, to thereby form a hollow tube open at both ends, as will be appreciated by persons skilled in the art.

The electrodes 1*a*, 1*b* can be formed from a range of good electrically conducting materials such as silver, nickel or gold. The electrodes 1*a*, 1*b* are typically formed from a coating process such as brush-paint, screen printing, spray, sputter or other methods. The electrodes 1*a*, 1*b* should be adhesive enough to inhibit from peeling off during work. In general this is preferably achieved by cofiring the electrodes 1a, 1b with the piezoelectric tube 1i, although other techniques may also be used.

Preferably the electrodes 1a, 1b should be as thin as possible, with the maximum thickness not exceeding 200 μm. Similarly, the gap 1e should be as narrow as possible, and is preferably below 0.5 mm.

After coating the electrodes 1a, 1b onto the surfaces of the tube 1i, the piezoelectric transducer should be poled along the thickness direction under electric field, as will be appreciated by those skilled in the art. For PZT or modified PZT materials, typical poling conditions would include the application of an electrical field in the region of 2~4 kV/mm, for between 20~120 minutes duration and at temperature 100 to 150° C. This may be performed in silicon oil.

In use, electric signals generated by a control system (which will be described in more detail below) are applied to the outer electrode 1a using wires 1c. The wires 1c can be connected to the transducer using an electrically conducting epoxy resin, or the like, after poling, or by soldering the wires to the outer electrode 1a before poling.

A ground connection wire (not shown) is also applied to the inner 1b electrode in a similar manner. In this case, the position at which the ground wire is connected is not important.

The wires 1c are preferably connected to the outer electrode 1a at the nodal positions 1d, which are situated at 0.23 times the length of the tube 1i (i.e. 0.23×1i), as shown. The reason for this is that the tube will operate to flex and vibrate in use, as will be explained in more detail below. At the nodal position 1d, the net displacement and hence strain during the flexing procedure will be reduced. Thus, the wire will experience reduced displacement and strain if positioned at the nodal location, which helps ensure that the connection between the wire and the outer electrode 1a does not break due to undue strains.

It will be appreciated that a number of different designs of inducer may be used with the transducer described above, depending on factors such as the implementation and the purpose for which the pump is being used.

Figure 3A:
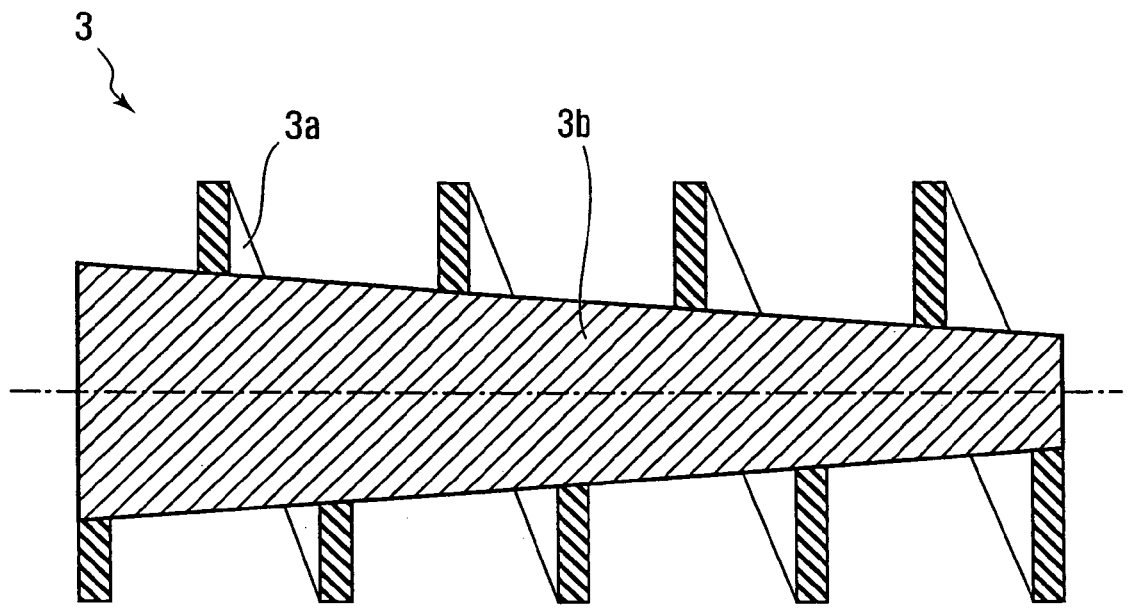
FIG. 3A is a cross sectional view of an example of a male type axial inducer.
Figure 3B:
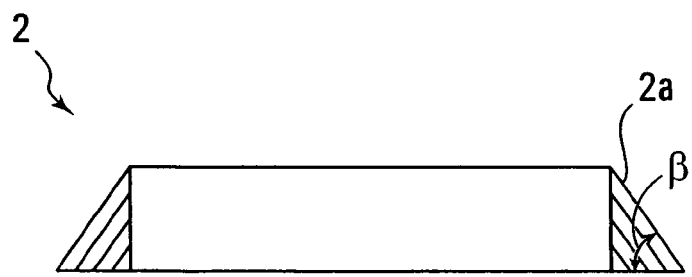
FIG. 3B is a cross sectional view of an end cap for use with the inducer of FIG. 3A.
Figure 3C:
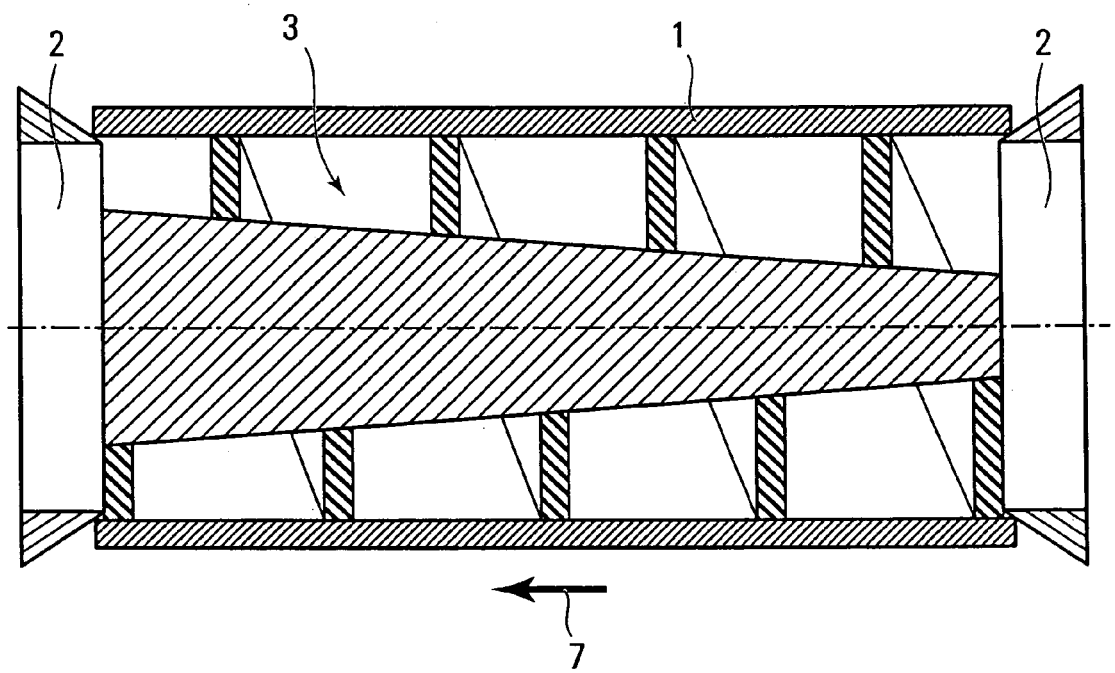
FIG. 3C is a cross sectional view of the inducer of FIG. 3A coupled to the transducer of FIG. 2.

A first example of an inducer, known as a male design, is shown in FIGS. 3A to 3C.

In this example, the inducer is formed from a blade 3a coupled to a shaft 3b. As shown, the blade extends radially outwardly from the shaft, and extends circumferentially around, and along the shaft, so as to define a thread.

In use, each end of the shaft 3b is coupled to a respective end cap 2, an example of which is shown in FIG. 3B. The end caps 2 are used to couple retain the shaft in position within the transducer body 1i, as shown for example in FIG. 3C. In this example, the retaining nut 4 and the spring 5 are omitted for clarity.

Accordingly, it will be appreciated that rotation of the inducer will cause fluid contained within the body 1i to be urged in the direction parallel to the shaft 3b, as shown by the arrow 7.

The inducer 3 is preferably configured such that there is a change in volume experienced by the fluid along the length of the inducer, resulting in the urging action. In particular, as the volume increases along the inducer path, the fluid pressure decreases, thereby causing fluid flow from the higher-pressure (lower volume) regions to the lower pressure (higher volume) regions.

This change in pressure can be achieved by either increasing the pitch, and/or tapering the shaft. In the example, shown in FIG. 3C, the pitch increases from top to bottom (such that there is a greater pitch at the bottom of the inducer as viewed in FIG. 3), and accordingly, in this example, the fluid is urged in the direction of the arrow 7.

However, if the volume gradient along the length of the inducer becomes too great, this will lead to flow that becomes turbulent and unstable. Accordingly, in this example, the change in pitch is used to induce a large volume change, with the taper configuration being used to smooth the pressure gradient along the inducer.

In general, flow can be induced in either direction by reversing the direction of rotation of the inducer. However, in the reverse direction, the flow will not benefit from the variations in pressure along the inducer, and accordingly, the flow will be less efficient.

The blade is preferably designed to be as thin as possible to thereby reduce the impact of rotational forces generated by rotation of the blade on the fluid. This inhibits the generation of vortices within the fluid being pumped. Generally a blade thickness of below 0.5 mm is preferred.

In general the end caps, shaft and blade may be formed from any material, and are typically prepared by machining or moulding. For ease of construction and durability, it is preferred to use materials that are elastic, have a low density, and are durable, such as plastics, aluminum alloys, stainless steel or the like. Alternatively, materials such as ceramics may be used.

In use, mechanical engagement between the end caps and the transducer is used to cause the rotational motion of the inducer, as will be explained in more detail below. Accordingly, it is preferable that the end cap surface 2a, which contacts the transducer, has a high coefficient of friction, and is highly polished, to ensure a smooth contact. Furthermore, it is preferred that the angle β (cone angle) is between 60° and 70° to increase the mechanical engagement of the end cap and the transducer.

However, alternative mechanisms for ensuring rotation of the inducer can be used. Thus for example, the end cap and the transducer tube can be profiled, such that the end cap surface 2a and the transducer are coupled by the profile. In general, the form of this profiling is calculated to increase engagement between the end cap and the transducer, thereby ensuring efficient rotation of the end cap. Thus, for example, the profile may take the form of a saw-toothed profile on the end cap surface 2a, or on the end of the transducer 1, with corresponding projections being provided on the end of the transducer of the end cap surface 2a.

Figure 4A:
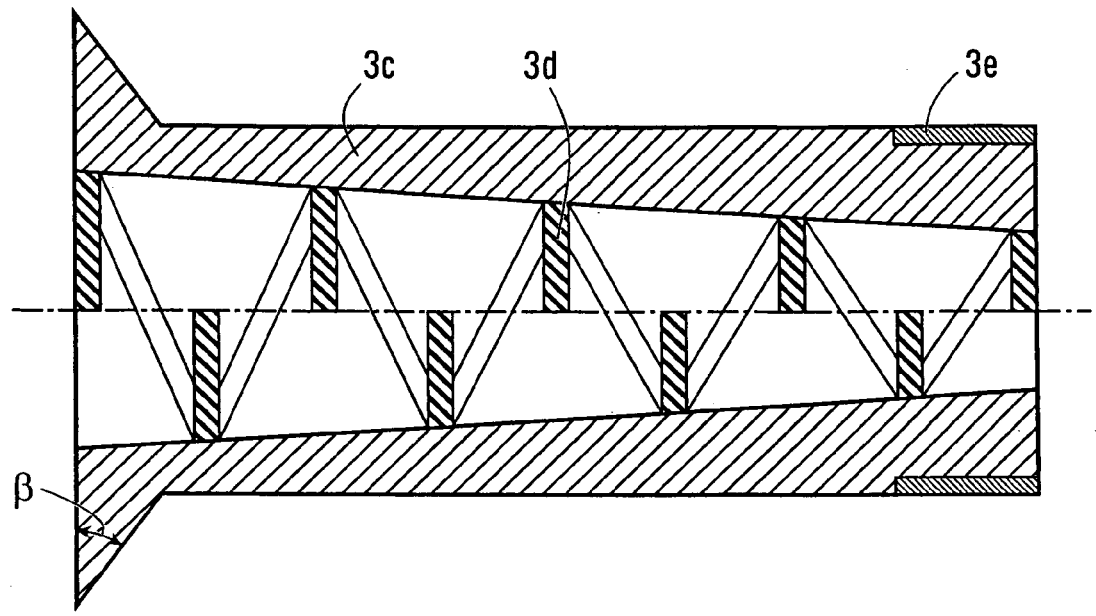
FIG. 4A is a cross sectional view of a first example of a female type axial inducer.
Figure 4B:
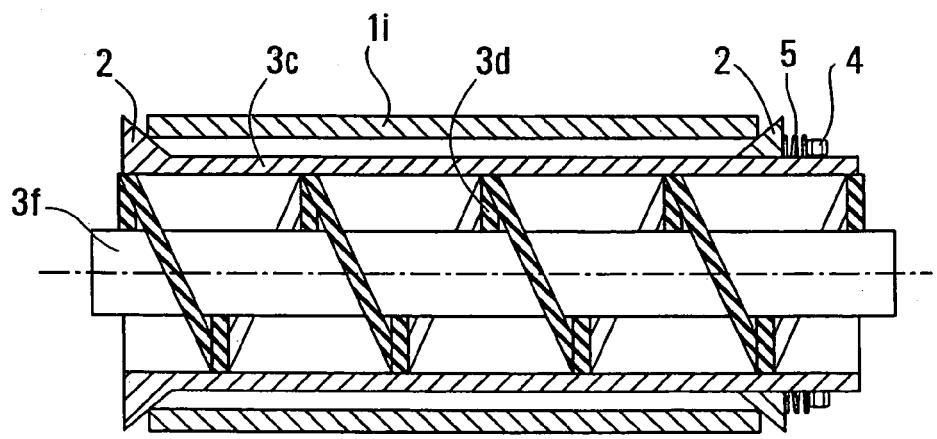
FIG. 4B is a cross sectional view of a second example of a female type axial inducer coupled to the transducer of FIG. 2.

Second and third examples of inducers, known as a female designs, are shown in FIGS. 4A and 4B.

In the example of FIG. 4A, the inducer is formed from a shaft in the form of a cylinder 3c, having a blade 3d positioned therein. As shown, the blade 3d extends radially inwardly from the cylinder, and extends circumferentially around, and along the cylinder, so as to define a thread.

In the example of FIG. 4B, the inducer again includes a cylinder 3c, having a blade 3d positioned therein, with the blade spiraling along the inside of the cylinder to define a thread. In this case, the blade is also provided on a central shaft 3f, which can aid in the production of the inducer.

Again, the materials applied can be plastics, aluminum alloys, stainless steel, ceramics or the like. However, they are preferred to be elastic, low density, durable and of high frictional coefficient. All the components can be prepared by machining or molding.

The cylinder may be tapered, although as shown in the example of FIG. 4B, this is not essential. Again, the blade 3d may have a gradually varied pitch to aid in the generation of a compressive force for driving the fluid in a direction parallel to the cylinder axis.

In the example shown in FIG. 4A, a screw thread 3e is provided to allow a second end cap 2 to be coupled to the cylinder with the spring 5 and the retaining nut 4, as also shown in FIG. 4B.

In use, the spring is used to ensure that mechanical engagement is maintained between the end caps and the transducer at all times. In general, springs having a spring constant of between 0.005 and 0.02 kg/mm can be used applied. However, it will be appreciated that other means of ensuring engagement between the end caps and the transducer may also be used.

Figure 5:
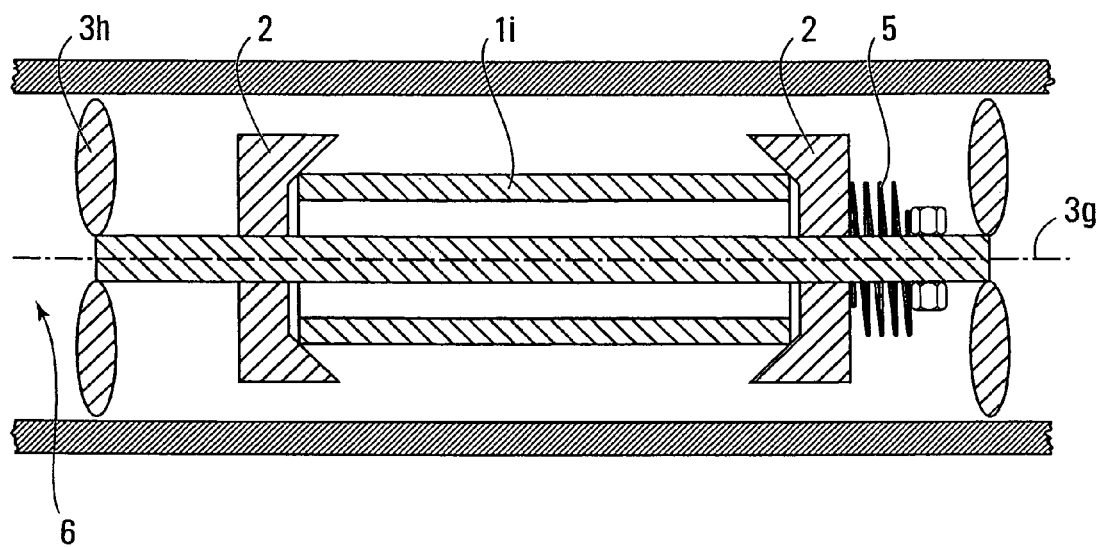
FIG. 5 is a cross sectional view of an example of an external inducer coupled to the transducer of FIG. 2.

In the examples described above, the inducers are fitted inside the transducer. As a result, the transducer body 1i can be adapted to form a flow path, along which the fluid is pumped. However, alternatively, the inducer may be provided externally to the transducer. An example of this is shown in FIG. 5.

In this example, the inducer is formed from a shaft 3g, having blades 3h mounted thereon. In use, the shaft 3g is again coupled to the transducer, using respective end caps 2, held in place by a spring 5 and retaining nut 4, as shown.

In this example, the transducer 1, and the inducer 3 are positioned in a flow path 6, such that rotation of blades 3h causes the fluid to be urged along the flow path, as will be appreciated by persons skilled in the art.

Operation of the transducer will now be described in more detail with respect to FIGS. 6A to 6C.

Figure 6A:
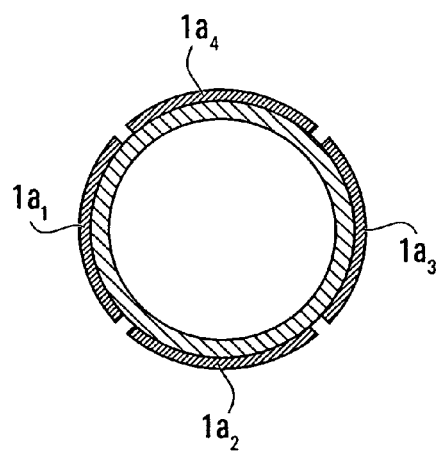
FIG. 6A is a plan view of the electrodes of the transducer of FIG. 2.
Figure 6B:
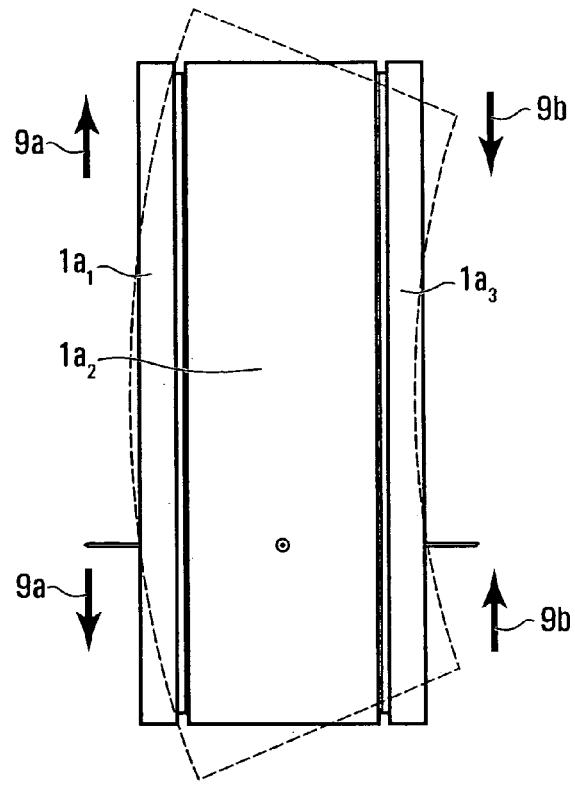
FIG. 6B is a schematic side view of the deformation transducer of FIG. 2.

As shown in FIGS. 6A and 6B, if opposing electrical signals are applied to the electrode portions 1a1, 1a3, this will cause the body 1i to expand in the region of the electrode portion 1a1, as shown by the arrows 9a. Similarly, the body will contract in the region of the electrode portion 1a3, as shown by the arrows 9b, (or vice versa, depending on the polarity of the signals), as shown by the dotted line in FIG. 6B. Similar effects will be obtained by the application of electrical signals to the electrode portions 1a2, 1a4.

From this, it will be appreciated that the application of appropriately selected electrical signals can be used to cause selective deformation of the body 1i. In particular, in the present example in which four electrode portions are provided, the application of four alternating signals to the electrode portions 1a1, 1a2, 1a3, 1a4, that are respectively 90° out of phase, will cause an oscillatory motion of the transducer in which the ends of the transducer will trace out substantially circular paths.

Figure 6C:
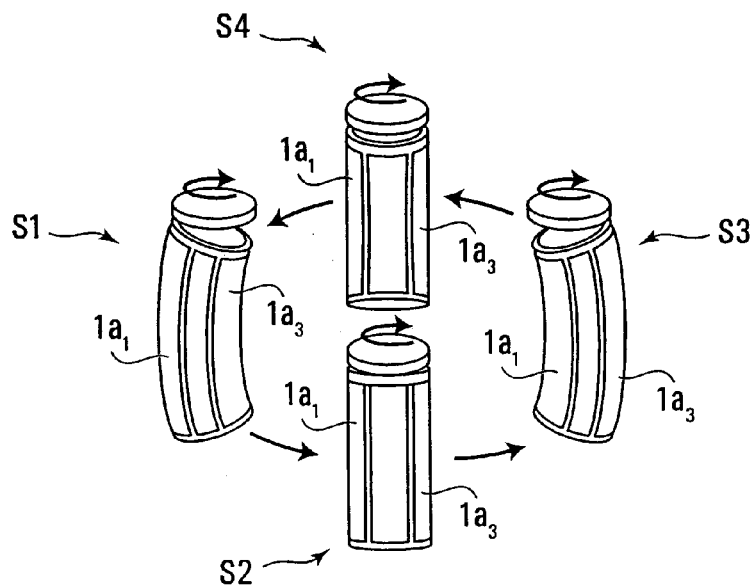
FIG. 6C is a sequence showing the deformation transducer of FIG. 2.

Thus as shown in FIG. 6C, at S1, a first positive signal is applied to the electrode portion 1a1, with a negative signal being applied to the electrode portion 1a3, and no signals being applied to the electrode portions 1a2, 1a4. This causes the transducer to bend towards the right hand side of FIG. 6C.

At S2, a positive signal is applied to the electrode portion 1a2, with a negative signal being applied to the electrode portion 1a4, and no signals being applied to the electrode portions 1a1, 1a3, thereby causing the transducer to bend into the page.

Similarly at S3, a positive signal is applied to the electrode portion 1a3, with a negative signal being applied to the electrode portion 1a1, and no signals being applied to the electrode portions 1a2, 1a4, thereby causing the transducer to bend towards the left.

Finally at S4, a positive signal is applied to the electrode portion 1a4, with a negative signal being applied to the electrode portion 1a2, and no signals being applied to the electrode portions 1a1, 1a3, thereby causing the transducer to bend out of the page.

Repeated deformation of the transducer in this manner causes the ends of the transducer to effectively jiggle in a rotational movement. As a result, there will always be a single point of contact between the end cap and the transducer, notably in the region of the electrode portion that is currently expanded (i.e. the electrode portion which has a positive signal applied thereto in the example outlined above).

By applying signals in sequence as described above, the point of contact for the transducer will move around the transducer end, as the ends of the transformer trace out the circular path. However, engagement between the end caps 2 and the transducer 1 (which may be frictional or mechanical) results in the end caps being rotated, as shown by the arrows 8.

Accordingly, the application of suitable alternating electrical signals having a phase difference of 90° to the electrode portions $1a_1$, $1a_2$, $1a_3$, $1a_4$, will cause the end cap and hence the inducer 3 to rotate. Furthermore the frequency of the signals will control the rate at which the rotation occurs, thereby allowing the rate at which fluid is pumped to be adjusted.

Figure 7:
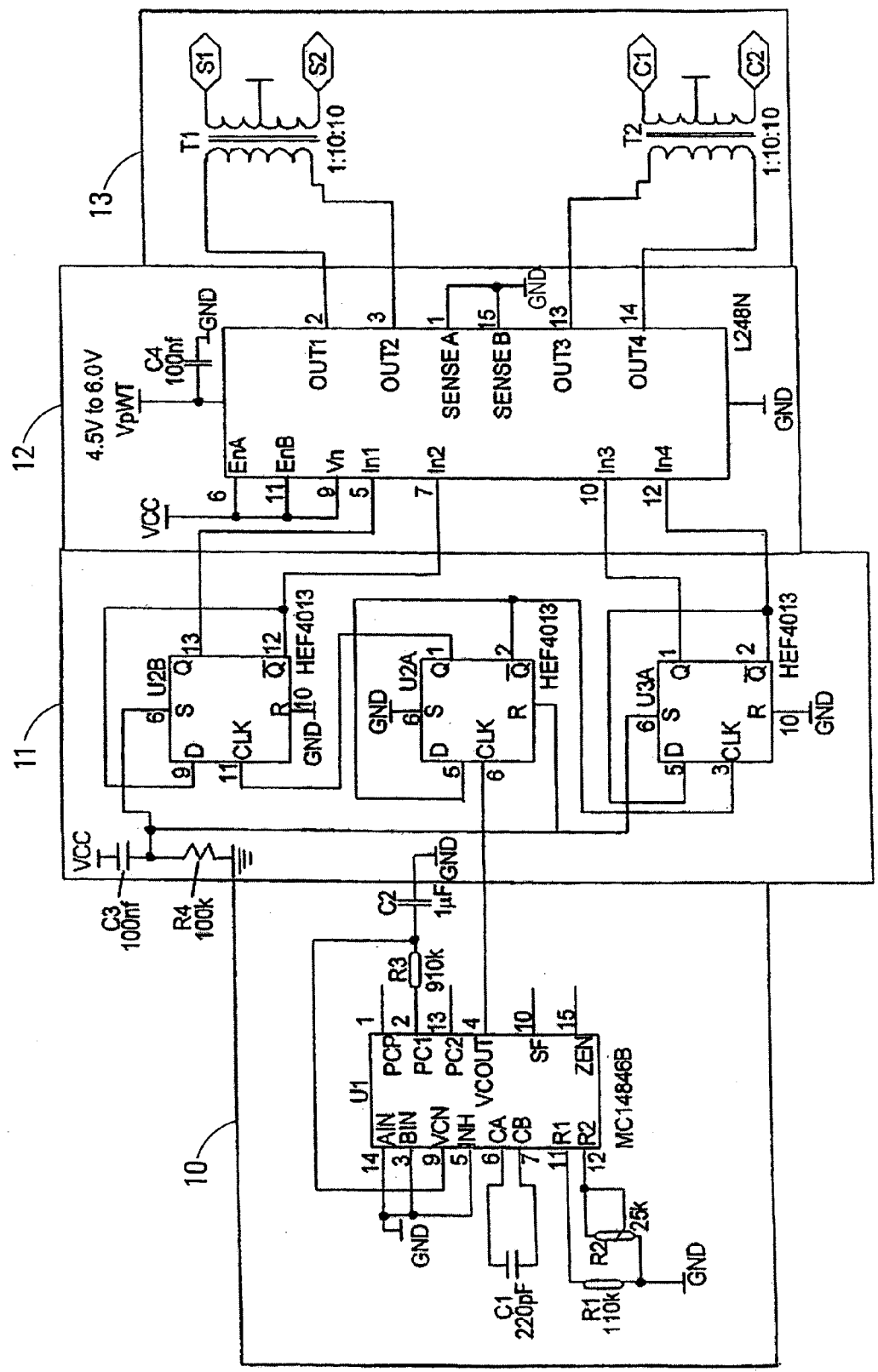
FIG. 7 is a circuit diagram of a controller for controlling the operation of the transducer of FIG. 2.

One embodiment of a circuit suitable for use as a power source is shown in FIG. 7. As will be appreciated by those skilled in the art, the circuit shown in FIG. 7 includes a frequency generator 10, coupled to a phase shifter 11, a current amplifier 12, and a voltage step-up circuit 13.

In use, the frequency generator operates to generate a digital oscillating signal having a frequency, the value of which is set by adjusting the variable resistor R2, as will be appreciated by those skilled in the art.

The signal is output to the phase shifter 11, which uses three D-type flip-flops to output four signals each of which are separated by 90°. In particular, this is achieved by using the digital signal output from the frequency generator to act as a clock signal for a first one of the flip-flops, which is configured to acts as a bistable flip-flop, thereby switching between two alternate states each time a clock signal is received. The Q and Q' outputs of the first flip-flop are used in turn to clock the remaining two flip-flops, which are also configured in bistable states.

Accordingly, the phase shifter outputs four digital signals having the predetermined frequency and which are offset by 90° with respect to each other.

The current amplifier operates to convert the signals into analogue signals having a predetermined current, which are then in turn applied to the voltage step-up. As a result the voltage step-up circuit outputs four signals having a sufficient magnitude to induce the desired contraction/expansion in the body, and which are separated by 90°. The signals can then be applied to the electrode portions 1a1, 1a2, 1a3, 1a4, as described above.

In this example, the input to the power source is 8~20 V DC voltage. The output amplitude is 50~200 Vp-p with respect to the ground, which is applied to the inner electrode 1b. The power source offers a range of frequencies from 10 kHz to 200 kHz.

It will be appreciated by persons skilled in the art that other suitable power sources could also be used.

In any event, it will be appreciated that this allows the pump to operate at a controllable rate by suitable adjustment of the value of the resistance of resistor R2.

In the embodiment described above, four electrode portions 1a1, 1a2, 1a3, 1a4, are shown. However, other numbers of electrode portions may be provided. In order to induce the jiggling motion of the ends of the transducer, it will be necessary to have at least three electrode portions, although in general the more electrode portions that are provided, the more the motion of the transducer ends can be controlled.

In general, it is also preferable to have the electrode portions arranged in pairs, with each electrode portion in a respective pair being provided in circumferential opposition. The reason for this is to allow the electrode portions to cause expansion and contraction of the piezoelectric tube on opposite sides of the tube body 1*i*, thereby increasing the deformation of the tube. This aids in efficient transfer of the jiggling motion energy into rotational energy in the inducer 3.

The principle of controlling the signals applied to the electrode portions 1*a* will be adjusted depending on the number of electrode portions 1*a* used. Thus, for example, in the case of six electrode portions (arranged in three opposing pairs), six control signals would be applied, each of which is separated by 60° phase difference (with each electrode portion in a corresponding pair receiving signals phase separated by 180°).

Figure 8:
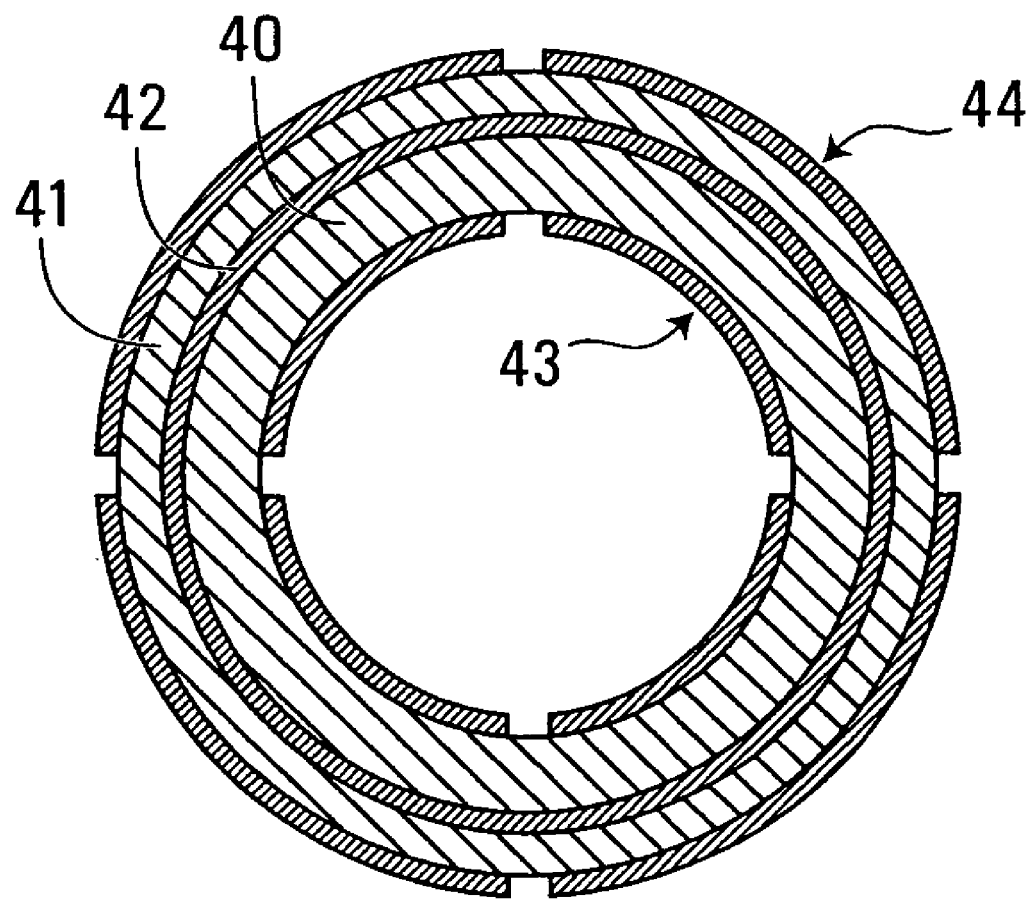
FIG. 8 illustrates an embodiment of a transducer formed from a double layered piezoelectric tube.

A development on the above is for the transducer to be formed from a double layered piezoelectric tube, an example of which is shown in FIG. 8. In this example the double-layered transducer includes first and second layers 40, 41 separated by an intermediate electrode 42 inner and outer electrodes 43, 44 are also provided and are sectioned into quadrants as shown. The fabrication process may be substantially similar to that mentioned above with respect to the single layer transducer.

Thus, in one embodiment, a suspension of piezoelectric ceramic particles can be deposited onto a rod using electrophoresis. The deposited layer is thoroughly dried before the outer surface is coated with a uniform layer of metallic paste, such as platinum paste. A second layer of deposition can be performed to produce a second ceramic layer.

The deposited layers are heat treated by heating in a furnace at between 500° C. and 1200° C., to thereby solidify the particle layer and burn away the rod, thereby a tube is formed from the intact particle layer. The tube is then sintered at temperatures between 850° C. and 1300° C. to form a dense ceramic tube.

The tube is then allowed to cool, before having the closed end removed, to thereby form a hollow tube open at both ends, as will be appreciated by persons skilled in the art.

In use, the intermediate electrode 42 is used as a ground, with positive and negative signals being applied to respective quadrants of the inner and outer electrodes 43, 44. This therefore requires additional control signals. However, it will be appreciated that this can be used to increase the bending displacement that can be achieved with the transducer, which can lead to an increased inducer rotation speed.

These techniques can be further applied to multi-layered tubes having a number of layers N (where N≧2). In this case, the tubes will be fabricated in a manner similar to that described above, with each additional layer being deposited over a respective intermediate electrode, such that for a tube having N layers, there are N−1 intermediate electrodes, with additional inner and outer electrodes being provided, as will be appreciated by those skilled in the art. The fabrication of such a tube is described in our copending application entitled "Piezoelectric Tubes" (filed as Ser. No. 60/416,505, filed Oct. 3, 2002) which is incorporated herein in its entirety by reference.

It will be appreciated that the use of a multi-layered tube can be used to further increase the bending displacement that can be achieved with the transducer, which can lead to further increased inducer rotation speeds.

A further embodiment is for the transducer tube shown in FIG. 2 to be used without the end caps 2, the inducer 3, the retaining nut 4, and the spring 5. In this case, the jiggling motion of the tube body 1*i* alone is used to induce motion of a fluid provided therein. In particular, the application of the excitation signals applied to causing selective contraction and/or expansion of the transducer body 1*i* can induce fluid motion.

The direction of motion of the fluid will generally depend on factors, such as the frequency of the rotational oscillation of the tube ends, the form of the compression and expansion, or the like.

In order to aid this, the inner surface of the tube body 1*i* can be profiled, to thereby help induce movement of the fluid. Thus, for example, the inner surface of the tube body 1*i* could be provided with a blade extending radially inwardly from the surface, and extending along the length of the tube in a spiral fashion (similar to the blade 3*d* provided in the inducer of FIG. 4A).

Finally, the electrode portions could be arranged circumferentially, allowing the fluid flow to be induced via a sequence of contractions or expansions of the tube diameter along the length of the tube in a manner similar to peristalsis.

Figure 9:
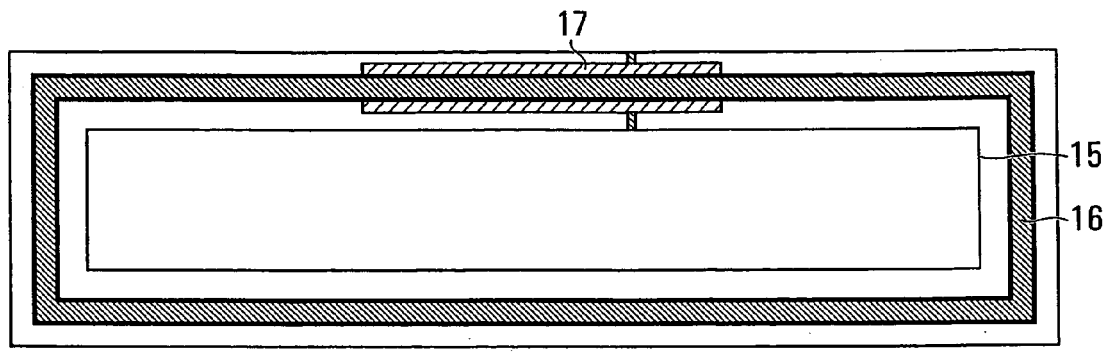
FIG. 9 is a schematic diagram of an example of the pump of FIG. 1 in use.

In use, the pump assemblies described above may be coupled to a flow path including fluid to be pumped. This is typically achieved by positioning the entire pump assembly 17, including the transducer 1 and the inducer 3 into a pipe 15 containing the fluid 16 to be pumped, as shown for example in FIG. 9.

The application of suitable electric fields can then be used to drive the fluid to flow in the pipe. The fluid will go through of the inside of the tubular transducer due to the pulling or pushing force generated by the axial inducer through rotation.

Figure 10:
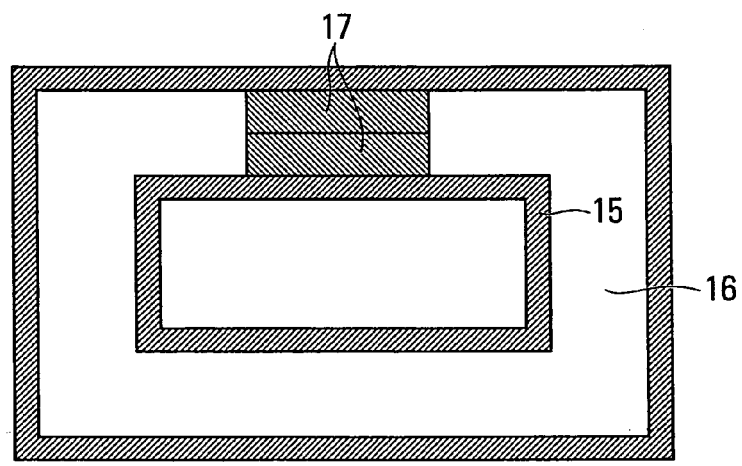
FIG. 10 is a schematic diagram of two of the pumps of FIG. 1 in use in parallel.
Figure 11:
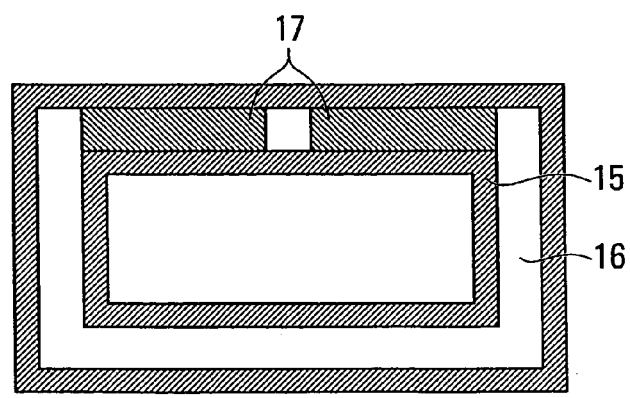
FIG. 11 is a schematic diagram of two of the pumps of FIG. 1 in use in series.

A number of pumps can be provided in a single flow path, for example by arranging the pumps in parallel, as shown for example in FIG. 10, or in series, as shown for example in FIG. 11, as will be appreciated by those skilled in the art.

Accordingly, the system described above provides an axial pump that pumps fluid in an axial direction using the piezoelectric effect of ferroelectric materials. It provides a very simple configuration with an excellent torque and rotational speed for delivery of fluid. In addition, it also has a relatively more gradual change of pressure for the fluid driving, hence is an excellent choice for biomedical applications.

In particular, one of the applications is to be used as a blood pump, which is a heart assist devices that is used to supplement the pumping ability of the ventricle, the heart's pumping chamber.

In this regard, the pump described above has a number of advantages, in that the pump will minimally induce vortices in the blood. The pump is also driven by piezoelectricity, thus no magnetic field generates and power consumption is low. It is hence minimally affected by the external magnetic fields and largely reduces the risk of mal-function due to external factors.

The dimension of the pump can be scaled according to the practical requirement. It is to be noted that the dimension of the pump can be reduced significantly compared with conventional electromagnetic pumps.

Thus, the invention example described above provides an axial pump that is simple, light weight and easy to manufacture.

It will be appreciated however, that the above technique could also be implemented using alternative transducers that do not use the piezoelectric effect. In particular, any material that can be induced to expand or contract under the application of a suitable signal can be used to construct a tubular transducer that is capable of performing the oscillatory motion outlined above, to thereby induce rotational movement in the inducer.

Thus, for example, the tube could be formed from a resilient but flexible material provided with muscle wire extending along the length of the tube in circumferentially spaced regions. In this case, application of a current to the muscle wire can cause the wire to contract, thereby causing the required deformation of the tube. In this instance, expansion is not possible and the technique is therefore slightly less efficient than that described above. However, it is only necessary to apply current to one of the regions at any one time, which can have benefits in the implementation of the control system.

It will be appreciated that the above described pump could have a number of applications beyond the medical field. Thus, general industrial applications that require a submergible pump will benefit significantly from the use of a pump of this form.

Furthermore reliability of the pump makes it ideal for use in environments where maintenance may be an issue, for example in space, or deep sea applications. Finally, the pump can be used in simple applications due to its low cost, such as pumping fluids in the beverage industry.

Persons skilled in the art will appreciate that numerous variations and modifications will become apparent. All such variations and modifications that become apparent to persons skilled in the art, should be considered to fall within the spirit and scope that the invention broadly appearing before described.

What is claimed is:

1. A fluid pump for pumping fluid, the fluid pump comprising:
    a flow path;
    a driver having:
    a substantially tubular shaped body defining a body axis; and,
    a number of elements circumferentially spaced around the body, each element being responsive to a signal to cause a corresponding portion of the body to expand or contract in a direction substantially parallel to the body axis; and,
    an urging member positioned in the flow path, the urging member being coupled to the driver such that selective expansion and contraction of the body causes the urging member to rotate, thereby urging fluid along the flow path in use;
    wherein the body is formed from piezoelectric material and the elements are piezoelectric elements each being formed from:
    a common electrode mounted on an inner surface of the body; and
    a respective electrode mounted on an outer surface of the body.

2. A pump according to claim 1, the elements extending substantially along the length of the body.

3. A pump according to claim 1, the body having a diameter of less than 0.1 m, and having a length of less than 1 m.

4. A pump according to claim 1, each electrode being formed from a metal film having a thickness of less than 0.001 m.

5. A pump according to claim 1, the pump further including a controller coupled to the elements, the controller being adapted to generate electrical signals thereby causing the selective expansion and contraction of the elements.

6. A pump according to claim 5, the elements being arranged in pairs, each pair being positioned in circumferential opposition, the controller being adapted to generate electrical signals to thereby selectively activate an element pair such that one of the elements expands and the other element contracts.

7. A pump according to claim 6, the controller being adapted to activate each element pair in turn, to thereby cause the elements to expand and contract in a circumferential sequence.

8. A pump according to claim 6, the controller being adapted to generate signals having a selected frequency, the signals being applied to each element in the element pair having a phase difference of 180°.

9. A pump according to claim 8, the controller being coupled to a DC power source to receive an input signal of up to 1000 V, the controller being adapted to generate signals of between 1 to 10000 $V_{p-p}$ and a selected frequency of up to 40 MHz.

10. A pump according to claim 1, the urging member including:
    a shaft defining a shaft axis that extends along the flow path; and,
    a blade extending radially from the shaft, the blade extending circumferentially around the shaft and along the shaft axis, such that rotation of the shaft causes the blade to urge fluid in a direction substantially parallel to the shaft axis.

11. A pump according to claim 10, the blade extending along the shaft so as to define a thread, the pitch of the thread varying along the length of the shaft.

12. A pump according to claim 10, the shaft being substantially tubular, and the blade extending radially inwardly toward the shaft axis.

13. A pump according to claim 10, the shaft being substantially cylindrical, the blade extending radially outwardly from the shaft.

14. A pump according to claim 10, the shaft being tapered.

15. A pump according to claim 10, the urging member further including end caps for coupling the shaft to the driver.

16. A pump according to claim 15, each end cap having a substantially frustroconical shape, having a cone angle of between 60° and 70°.

17. A pump according to claim 15, the end caps being coupled to the shaft such that the end caps are urged against ends of the piezoelectric elements.

18. A pump according to claim 15, at least one of the end caps being coupled to the shaft by a resilient member, the resilient member being adapted to urge the end cap against a respective end of the piezoelectric elements.

19. A pump according to claim 18, the resilient member being a spring having a spring constant of between 0.005 and 0.02 kg/mm.

20. A pump according to claim 1, the pump being adapted to be coupled to a circulatory system to pump blood.

21. A fluid pump for pumping fluid, the fluid pump comprising:
    a flow path;
    a driver having:
    a substantially tubular shaped body defining a body axis; and, a number of elements circumferentially spaced around the body, each element being responsive to a signal to cause a corresponding portion of the body to expand or contract in a direction substantially parallel to the body axis; and, an urging member positioned in the flow path, the urging member being coupled to the driver such that selective expansion and contraction of the body causes the urging member to rotate, thereby urging fluid along the flow path in use;

wherein the elements are piezoelectric elements, the body being formed from a double layered piezoelectric material, each piezoelectric element being formed from:

a common electrode positioned between the layers;

a first set of respective electrodes mounted on an inner surface of the body; and, a second set of respective electrodes mounted on an outer surface of the body.

22. A fluid pump for pumping fluid, the fluid pump comprising:

a flow path; and a driver having:

a substantially tubular shaped body defining a body axis; and, a number of elements circumferentially spaced around the body, each element being responsive to a signal to cause a corresponding portion of the body to expand or contract in a direction substantially parallel to the body axis, the driver being arranged in the flow path such that selective expansion and contraction of the body urges fluid along the flow path in use;

wherein the body is formed from piezoelectric material and the elements are piezoelectric elements each being formed from;

a common electrode mounted on an inner surface of the body; and a respective electrode mounted on an outer surface of the body.

23. A pump according to claim 22, the elements extending substantially along the length of the body.

24. A pump according to claim 22, the body having a diameter of less than 0.1 m, and having a length of less than 1 m.

25. A pump according to claim 22, the body being formed from a double layered piezoelectric material, each piezoelectric element being formed from:

a common electrode positioned between the layers;

a first set of respective electrodes mounted on an inner surface of the body; and, a second set of respective electrodes mounted on an outer surface of the body.

26. A pump according to claim 22, each electrode being formed from a metal film having a thickness of less than 0.001 m.

27. A pump according to claim 22, the pump further including a controller coupled to the elements, the controller being adapted to generate electrical signals thereby causing the selective expansion and contraction of the elements.

28. A pump according to claim 27, the elements being arranged in pairs, each pair being positioned in circumferential opposition, the controller being adapted to generate electrical signals to thereby selectively activate an element pair such that one of the elements expands and the other element contracts.

29. A pump according to claim 28, the controller being adapted to activate each element pair in turn, to thereby cause the elements to expand and contract in a circumferential sequence.

30. A pump according to claim 28, the controller being adapted to generate signals having a selected frequency, the signals being applied to each element in the element pair having a phase difference of 180°.

31. A pump according to claim 30, the controller being coupled to a DC power source to receive an input signal of up to 1000 V, the controller being adapted to generate signals of between 1 to 10000 $V_{p-p}$ and a selected frequency of up to 40 MHz.

32. A fluid pump according to claim 1, wherein the piezoelectric elements comprise a plurality of layers; and a plurality of electrodes arranged with respect to the layers of the piezoelectric elements such that at least an intermediate electrode contacts adjacent surfaces of the layers of the piezoelectric elements and outer electrodes contact exterior surfaces of the layers of the piezoelectric elements.

* * * * *

UNITED STATES PATENT AND TRADEMARK OFFICE
CERTIFICATE OF CORRECTION

PATENT NO. : 7,118,356 B2
APPLICATION NO. : 10/611306
DATED : October 10, 2006
INVENTOR(S) : Jan Ma et al.

It is certified that error appears in the above-identified patent and that said Letters Patent is hereby corrected as shown below:

COLUMN 2
Line 41 delete "Vp-p" and insert -- $V_{p\text{-}p}$ --

COLUMN 4
Line 32, delete "250 mm;" and insert --250 mm.--
Line 46 delete "BaTiO3" and insert --$BaTiO_3$--

COLUMN 5
Line 28 delete "(i.e. 0.23xli)" and insert --(i.e. 0.23x1f)--

COLUMN 7
Line 29 delete "1a1, 1a3" and insert -- $la_1$, $1a_3$ --
Line 31 delete "1a1" and insert --$1a_1$--
Line 33 delete "1a3" and insert --$1a_3$--
Line 36 delete "1a2, 1a4" and insert --$1a_2$, $1a_4$--
Line 42 delete "1a1, 1a2, 1a3, 1a4" and insert --$1a_1$, $1a_2$, $1a_3$, $1a_4$--
Line 47 delete "1a1" and insert --$1a_1$--
Line 48 delete "1a3" and insert --$1a_3$--
Line 49 delete "1a2, 1a4" and insert --$1a_2$, $1a_4$--
Line 53 delete "1a2" and insert --$1a_2$--
Line 54 delete "1a4" and insert-- $1a_4$--
Line 55 delete "1a1, 1a3" and insert --$1a_1$, $1a_3$--
Line 58 delete "1a3" and insert --$1a_3$--
Line 59 delete "1a1" and insert --$1a_1$--
Line 60 delete "1a2, 1a4" and insert--$1a_2$, $1a_4$--
Line 63 delete "1a4" and insert --$1a_4$--
Line 64 delete "1a2" and insert --$1a_2$--
Line 65 delete "1a1, 1a3" and insert --$1a_1$, $1a_3$--

COLUMN 8
Line 18 delete "cap" and insert --caps 2--
Line 51, delete "1a1, 1a2, 1a3, 1a4" and insert --$1a_1$, $1a_2$, $1a_3$, $1a_4$--
Line 54 delete "Vp-p" and insert -- $V_{p\text{-}p}$--
Line 64 delete "1a1, 1a2, 1a3, 1a4" and insert --$1a_1$, $1a_2$, $1a_3$, $la_4$--

UNITED STATES PATENT AND TRADEMARK OFFICE
CERTIFICATE OF CORRECTION

PATENT NO. : 7,118,356 B2
APPLICATION NO. : 10/611306
DATED : October 10, 2006
INVENTOR(S) : Jan Ma et al.

It is certified that error appears in the above-identified patent and that said Letters Patent is hereby corrected as shown below:

COLUMN 13
Line 31 delete "from;" and insert --from:--

Signed and Sealed this

Third Day of April, 2007

JON W. DUDAS
*Director of the United States Patent and Trademark Office*